United States Patent [19]

Carobbi et al.

[11] Patent Number: 4,957,564
[45] Date of Patent: Sep. 18, 1990

[54] PROCESS FOR PREPARING LACTULOSE FROM LACTOSE BY EPIMERIZATION WITH SODIUM ALUMINATE

[75] Inventors: Renato Carobbi, Pistoia; Franco Innocenti, Bagno A Ripoli, both of Italy

[73] Assignee: SIRAC S.r.l., Italy

[21] Appl. No.: 272,445

[22] Filed: Nov. 17, 1988

[30] Foreign Application Priority Data

Dec. 1, 1987 [IT] Italy ................................ 22847 A/87

[51] Int. Cl.$^5$ ........................ C13K 13/00; C13D 3/14; C13D 3/00
[52] U.S. Cl. .................................... 127/46.3; 127/48; 127/50; 536/125; 536/127; 423/119; 423/600
[58] Field of Search ........................... 127/46.3, 48, 50; 536/124, 125, 127; 426/271, 658; 423/600, 119

[56] References Cited

U.S. PATENT DOCUMENTS 3,546,206 12/1970 Guth et al. ........................... 536/125
3,822,249 7/1974 Tumerman et al. ................ 536/125

OTHER PUBLICATIONS

*Chemical Abstracts,* v. III, No., Aug. 21, 1989, p-Chemical Abstract No. 59888j, Carobbi et al., "Process for Preparing Lactulose from Lactose by Epimerization with Sodium Aluminate," Eur. Pat. Appl. No. 320,670, Jun. 21, 1989.

*Primary Examiner*—Chung K. Pak
*Attorney, Agent, or Firm*—Arnold, White & Durkee

[57] ABSTRACT

A process for preparing lactulose from lactose in which an aqueous lactose mixture is reacted with a sodium aluminate solution and the solution obtained is continuously neutralized by feeding this solution and a sulphuric acid solution to a reactor simultaneously in such a manner as to obtain a pH of between 4.5 and 8.

By operating in this manner an aluminium hydroxide suspension is obtained which can be easily separated from the lactulose solution.

10 Claims, No Drawings

PROCESS FOR PREPARING LACTULOSE FROM LACTOSE BY EPIMERIZATION WITH SODIUM ALUMINATE

FIELD OF THE INVENTION

This invention relates to a process for producing lactulose by epimerizing lactose by the action of sodium aluminate, which can be implemented on an industrial scale.

PRIOR ART

Lactulose is a synthetic disaccharide currently used in syrup form for the treatment of intestinal affections and in crystalline form as a sweetener replacement for saccharin. It is also used as a food supplement in pediatric and geriatric diets.

Many processes for preparing lactulose by epimerization of lactose are known, this latter being a widely available natural disaccharide.

Some of these processes are based essentially on the epimerization of lactose by means of strong alkalis such as $Ca(OH)_2$, NaOH, KOH and strong organic bases.

These processes have the drawback of leading to the formation of a considerable percentage of difficulty separable, coloured by-products which strongly reduce the lactulose yield and make it difficult both to use the lactulose in its syrup form and to prepare it as a crystalline product.

Another group of processes uses sodium tetraborate and sodium aluminate as epimerization agents.

Although these processes give a higher lactulose yield and a purer product, they are unsatisfactory from the industrial aspect both because of the difficulty of filtering off the aluminum hydroxide and because of the difficulty of quantitatively eliminating the boric acid.

Other processes using strongly alkaline ion exchange resins for the epimerization are too costly and do not enable lactulose to be produced at market prices.

Processes for lactulose epimerization by magnesium compounds are also known.

These processes have the drawback of requiring very high reaction volumes to obtain small quantities of lactulose.

SUMMARY OF THE INVENTION

We have now discovered a lactulose production process by which the drawbacks of the known art are obviated.

In particular, we have discovered a process involving epimerization of lactose by sodium aluminate which enables the aluminium hydroxide to be easily filtered off and the sodium aluminate to be easily recovered for use in the next cycle.

The process of the present invention is characterised by being conducted in the following steps:

(a) forming an aqueous mixture of lactose with sodium aluminate;

(b) continuously neutralizing the solution obtained from step (a) by feeding said solution and a sulphuric acid solution to a reactor simultaneously;

(c) separating the aluminium hydroxide by a centrifugal decanter;

(d) subjecting the solution obtained from step (c) to ultrafiltration or microfiltration;

(e) deionizing the solution obtained from step (d);

(f) concentrating the solution obtained from step (e) to a concentration of about 50% of lactulose by weight;

(g) treating the solids obtained from steps (c) and (d) with a NaOH solution;

(h) calcining the product of step (g) to obtain sodium aluminate, which is recycled to step (a).

DETAILED DESCRIPTION OF THE INVENTION

To prepare lactulose by the process of the present invention, a mixture of lactose and water is firstly prepared in a suitable mixer using a water:lactose weight ratio of between 2:1 and 4:1.

This mixture is fed into a reactor together with a 35-45% w/w sodium aluminate solution, after which the mass is homogenized by agitation and reacted at a temperature of between 50° and 70° C. for a time of between 30 and 60 minutes.

The sodium aluminate is used in a weight ratio to the lactose of between 0.3:1 and 1:1.

The solution obtained from the reaction with sodium aluminate is fed continuously, simultaneously with a sulphuric acid solution of concentration between 3N and 5N, to a neutralization reactor using such feed rates as to obtain a residence time of between 20 and 60 minutes. The feed ratio is controlled to obtain neutralization to a pH of between 4.5 and 8 and preferably between 6 and 7.

In this respect we have found that if neutralizing to less than pH 4.5 a gelatinous mass forms which is impossible to filter off, whereas if neutralizing to more than pH 8 the aluminium hydroxide precipitation is incomplete. By neutralizing to pH 4.5-8 the precipitate characteristics are such that its suspension is sufficiently fluid to allow simple filtration.

The suspension obtained in the neutralization step is separated by centrifugal decanting to obtain a solid with a dry material content of about 30% by weight and a liquid containing a small quantity of suspended aluminium hydroxide.

This liquid is subjected to ultrafiltration or microfiltration to separate the suspended aluminium hydroxide. A perfectly clear solution is obtained and is deionized by ion exchange resins in accordance with known processes after which it is concentrated to obtain the required lactulose syrup, having the following composition weight:

| lactulose: | 45-55% |
| lactose: | 1-3% |
| galactose: | 2-6% |

The solids from the centrifugal decantation and ultrafiltration steps are pooled, treated with 48% w/w sodium hydroxide until pH 11-12 is reached, and the mixture obtained is calcined at 700°-800° C. to burn off the contained organic compounds and recover the sodium aluminate, which is recycled to the first process step.

The following example is given for non-limiting illustration of the invention.

EXAMPLE 1

1000 kg of lactose are mixed with 3000 kg of water and fed into a reactor together with 1100 kg of a 40% w/w sodium aluminate solution.

The mixture is kept under agitation for 20 minutes after which the solution obtained is pumped through a continuous reactor at a throughput which gives it a retention time therein of 40 minutes, the temperature being kept constant at 60° C.

After this time, during which the reaction proceeds, the solution is fed continuously to a neutralization reactor while a 4N sulphuric acid solution is fed simultaneously to the same reactor, the throughputs of the two solutions being controlled so as to obtain a constant pH of 6.5.

A suspension is obtained containing 6.5% by weight of aluminium hydroxide and 12% by weight of lactulose.

Most of the aluminium hydroxide is separated in a centrifugal decanter to obtain an opalescent solution containing 0.7% of aluminium hydroxide by weight. This is removed by ultrafiltration.

The solution obtained is deionized by ion exchange resins of known type and is then concentrated to obtain 1250 kg of lactulose syrup having the following composition by weight:

| | | |
|---|---|---|
| lactulose: | 50% | |
| lactose: | 1.7% | |
| galactose: | 4.6% | |

The aluminium hydroxide from the centrifugal decanting and ultrafiltration steps is pooled and treated with a 48% w/w sodium hydroxide solution until pH 11.5 is obtained. The resultant solution is calcined at 750° C. to obtain 400 kg of 95% sodium aluminate which is recycled to a subsequent cycle.

We claim:

1. A process for preparing lactulose from lactose by epimerization with sodium aluminate, comprising the following steps:
    (a) reacting an aqueous mixture of lactose with sodium aluminate to form a solution containing lactulose;
    (b) continuously neutralizing the solution obtained from step (a) by feeding said solution and a sulphuric acid solution to a reactor simultaneously;
    (c) separating the aluminum hydroxide by a centrifugal decanter;
    (d) subjecting the solution obtained from step (c) to ultrafiltration or microfiltration;
    (e) deionizing the solution obtained from step (d);
    (f) concentrating the solution obtained from step (e) to a concentration of about 50% of lactulose by weight;
    (g) treating the solids obtained from steps (c) and (d) with a NaOH solution;
    (h) calcining the product of step (g) to obtain sodium aluminate which is recycled to step (a).

2. A process as claimed in claim 1, wherein the reaction between the aqueous lactose mixture and sodium aluminate is conducted at a temperature of between 50° and 70° C. for a time of between 30 and 60 minutes.

3. A process as claimed in claim 1, wherein the reaction between the aqueous lactose mixture and sodium aluminate is conducted with a sodium aluminate:lactose weight ratio of between 0.3:1 and 1:1.

4. A process as claimed in claim 1, wherein the aqueous lactose mixture is formed with a water:lactose weight ratio of between 2:1 and 4:1.

5. A process as claimed in claim 1, wherein said sodium aluminate is used in a 35–45% w/w solution.

6. A process as claimed in claim 1, wherein the continuous neutralization of the solution obtained from step (a) is effected with a 3N–5N concentration sulphuric acid solution, the throughputs being such as to obtain neutralization to a pH of 4.5–8.

7. A process as claimed in claim 1, wherein the continuous neutralization of the solution obtained from step (a) is effected with throughputs such as to obtain a retention time of 20–60 minutes.

8. A process as claimed in claim 1, wherein the treatment of the solids obtained from steps (c) and (d) is effected with 48% w/w sodium hydroxide solutions until a pH of 11–12 is reached.

9. A process as claimed in claim 1, wherein said calcining of the product of step (g) is conducted between 700° and 800° C.

10. A process as claimed in claim 6, wherein the solution obtained from step (a) is neutralized to a pH of 6–7.

* * * * *

UNITED STATES PATENT AND TRADEMARK OFFICE
CERTIFICATE OF CORRECTION

PATENT NO. : 4,957,564
DATED : September 18, 1990
INVENTOR(S) : Renato CAROBBI et al.

It is certified that error appears in the above-identified patent and that said Letters Patent is hereby corrected as shown below:

On the title page, [73] Assignee:, change "SIRAC Srl, Italy" to -- INALCO Spa, Italy--.

Signed and Sealed this

Thirtieth Day of March, 1993

Attest:

STEPHEN G. KUNIN

*Attesting Officer*  *Acting Commissioner of Patents and Trademarks*